US00PP11801P2

(12) United States Plant Patent
Zary

(10) Patent No.: US PP11,801 P2
(45) Date of Patent: Mar. 13, 2001

(54) GRANDIFLORA ROSE PLANT NAMED 'JACOLPUR'

(75) Inventor: Keith W. Zary, Thousand Oaks, CA (US)

(73) Assignee: Jackson & Perkins Wholesale, Inc., Medford, OR (US)

( * ) Notice: Under 35 U.S.C. 154(b), the term of this patent shall be extended for 0 days.

(21) Appl. No.: 09/255,074

(22) Filed: Feb. 22, 1999

(51) Int. Cl.[7] ..... A01H 5/00

(52) U.S. Cl. ..... Plt./131

(58) Field of Search ..... Plt./130, 131, 138, Plt./139

*Primary Examiner*—Howard J. Locker
(74) *Attorney, Agent, or Firm*—Klarquist Sparkman Campbell Leigh & Whinston, LLP

(57) ABSTRACT

Grandiflora rose plant having a vigorous, upright, well-branched growth habit with dark green, glossy foliage, resistance to rust and powdery mildew and large, red flowers having lighter color on petal reverse.

1 Drawing Sheet

1

The present invention relates to a new and distinct variety of rose plant of the grandiflora class which was originated by me by crossing the variety 'JACheir', U.S. Plant Pat. No. 9,397, with the variety 'JACsedi', U.S. Plant Pat. No. 9,172.

The primary objetive of this breeding was to produce a new rose variety combining the large flower size, deep flower color, strong fragrance, vigor, glossy foliage, and hybrid tea flower form of the female parent with the vigor, fragrance, healthy foliage, and well-branched habit of the male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright, well-branched growth;
2. Dark green, glossy foliage;
3. Good resistance to rust and powdery mildew;
4. Large flowers red in color;
5. Strong fragrance;
6. Petal reverse of a lighter color.

Asexual reproduction of this new variety by budding on Dr. Huey rootstalk, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultura l Society (London) Colour Chart, except where ordinary dictionary significance of color is indicated.

Parentage:

*Seed parent.*—'JACheir' U.S. Plant Pat. No. 9,397.

*Pollen parent.*—'JACsedi' U.S. Plant Pat. No. 9,172.

Classification:

*Botanical.*—*Rosa hydrida.*

*Commercial.*—Grandiflora.

2

FLOWER

Observations made from specimens grown in a garden environment at Somis, Calif., March 1997 to December 1998.

Blooming habit: Recurrent.

Bud:

*Size.*—One and three-quarter inches log when the petals start to unfurl.

*Form.*—The bud form is long, pointed ovoid.

*Color.*—When sepals first divide, bud color is Red Group 46A. When half blown, the upper sides of the petals are Red Group 53D on the outer two-thirds of the petals. The inner one-thirds are White Group 155B with some flecks of Red Group 53D. The lower sides of the petals are White Group 155B with a blush of Red Group 53D showing through the petal. This gives to the underside an overall color of Red-Purple Group 66D.

*Sepals.*—Color: Green Group 138B often with a blush of Red-Purple Group 181A in areas exposed to bright sun. Surface texture: Covered in fine hairs. There are three lightly appendaged sepals. There are two unappendaged sepals with hairy edges.

*Receptacle.*—Color: Green Group 137D often with a blush of Greyed-Red Group 181A in areas exposed to bright sun. Shape: Funnel. Size: Medium, about 7/16"×5/16". Surface: Smooth.

*Peduncle.*—Length: Medium to short, averaging about two and one-half inches to three inches. Surface: Smooth, with only an occasional gland. Color: Green Group 137D with Greyed-Red Group 178A in areas exposed to bright sun. Strength: Stiff, erect.

Bloom:

*Size.*—Large. Average open size is about five inches.

*Borne.*—Singly and several together in pyramidal clusters of three to seven blooms.

*Stems.*—Strength: Strong. Average length is about sixteen to twenty inches.

*Form.*—When first open: High-centered. Permanence: Retains its form to the end, outer petals curl back.

*Petalage.*—Number of petals under normal conditions: 30–35.

*Color.*—The upper sides of the petals are Red Group 53D on the outer two-thirds of the petal with White Group 155B on the inner third. The inner one-third also has flecks of Red Group 53D. The reverse sides of the petals are White Group 155D with Red Group 53D bleeding through the petals. This gives the overall color impression of Red-Purple Group 66D. The base of each petal has on the upper surface a 3/16"×1/4", Yellow Group 6D color spot. On the lower surface there is a 3/16"×3/16", Yellow Group 4C color spot. The major color on the upper side is Red Group 53D.

*Variegations.*—On both guard petals, petaloids and random petals, there are White Group 155D stripes. These occur on both surfaces.

*Discoloration.*—The general tonality at the end of the first day: No change. At the end of the third day: No change.

*Fragrance.*—Strong, lemon.

Petals:

*Texture.*—Thick.

*Shape.*—Round.

*Form.*—Tips slightly recurved.

*Arrangement.*—Imbricated. Petaloids in the center: Few (0–3), (1/4"×1/2" long×1/8" to 1/4" wide), Red Group 53D in color with an occasional White Group 155D streak.

*Persistence.*—Stay on plant until dry.

*Lastingness.*—On the plant: Fair (six to seven days). As a cut flower: Fair (about seven to eight days).

Reproductive parts:

*Anthers.*—Size: Medium. Quantity: Many. Color: Yellow-Orange Group 18C. Arrangement: Regular around styles.

*Filaments.*—Color: Yellow-White Group 158D.

*Pollen.*—Color: Yellow-Orange Group 19C.

*Styles.*—Color: Red-Purple Group 60C.

*Stigmas.*—Color: Yellow-White Group 158C.

Plant:

*Form.*—Bush.

*Growth.*—Vigorous, upright, branching. Mature plant height is about five to five and one-half feet, width is about three and one-half to four feet.

Foliage: Number of leaflets on normal mid-stem leaves: Five.

*Size.*—Large (7" long×5½" wide).

*Quantity.*—Abundant.

*Color.*—New foliage: Upper and lower surfaces: Greyed-Red Group 178A. Old foliage: Upper surface: Green Group 139A. Lower surface: Yellow-Green Group 147C.

Leaflets:

*Shape.*—Pointed oval.

*Texture.*—Leathery, glossy.

*Edge.*—Serrated.

*Serration.*—Single, small.

*Petiole rachis.*—Lower: Yellow-Green Group 147D. Upper: Greyed-Purple 183B.

*Petiole underside.*—Smooth with prickles.

*Stipules.*—Long (¾"), serrated, bearded.

*Disease resistance.*—Resistant to mildew and rust under normal growing conditions in a greenhouse. Susceptible to blackspot.

Wood:

*New wood.*—Color: Greyed-Red Group 178B. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Medium, hooked downward.

*Color when young.*—Greyed-Red Group 178B.

*Color when mature.*—Greyed-Orange Group 173D.

Small prickles:

*Quantity.*—On main stalks: None. On laterals: None.

I claim:

1. A new and distinct variety of rose plant of the grandiflora class, substantially as herein shown and described, characterized particularly by its vigorous, upright, well-branched growth with dark green, glossy foliage, resistance to rust and powdery mildew and its large, red flowers having lighter color on petal reverse.

* * * * *

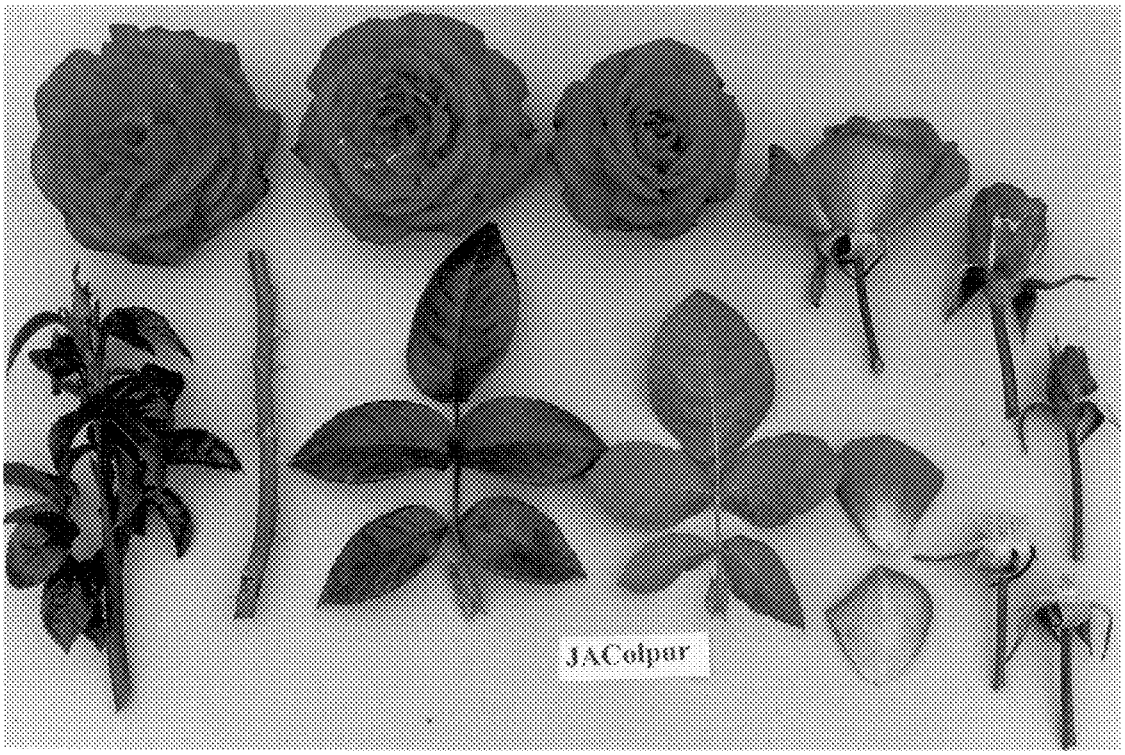
JAColpar